(12) United States Patent
Xu et al.

(10) Patent No.: US 6,673,588 B2
(45) Date of Patent: Jan. 6, 2004

(54) **METHOD FOR CLONING AND EXPRESSION OF MSPA1L RESTRICTION ENDONUCLEASE AND MSPA1L METHYLASE IN *E. COLI***

(75) Inventors: Shuang-yong Xu, Lexington, MA (US); Robert Maunus, Danvers, MA (US); Katy Stropnicky, St. Paul, MN (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 10/083,624

(22) Filed: Feb. 26, 2002

(65) Prior Publication Data

US 2003/0166206 A1 Sep. 4, 2003

(51) Int. Cl.[7] ............................. C12N 9/27; C12N 15/55
(52) U.S. Cl. .................. 435/199; 435/252.3; 435/320.1; 536/23.2
(58) Field of Search ............................. 435/199, 320.1, 435/252.3; 536/23.2

(56) References Cited

U.S. PATENT DOCUMENTS

| | | | |
|---|---|---|---|
| 5,200,333 A | 4/1993 | Wilson | 435/122.3 |
| 5,498,535 A | 3/1996 | Fomenkov et al. | 435/172.3 |

OTHER PUBLICATIONS

Roberts and Macelis, Nucl. Acids Res. 29:268–269 (2001).
Kosykh et al., Mol. Gen. Genet. 178: 717–719, (1980).
Mann et al., Gene 3: 97–112, (1978).
Walder et al., Proc. Natl. Acad. Sci. 78: 1503–1507, (1981).
Bougueleret et al., Nucl. Acids Res. 12: 3659–3676, (1984).
Gingeras and Brooks, Proc. Natl. Acad. Sci. USA 80: 402–406, (1983).
Theriault and Roy, Gene 19: 355–359 (1982).
Blumenthal et al., J. Bacteriol. 164: 501–509, (1985).
Wayne et al. Gene 202: 83–88, (1997).
Kiss et al., Nucl. Acids Res. 13: 6403–6421, (1985).
Szomolanyi et al., Gene 10: 219–225, (1980).
Janulaitis et al., Gene 20: 197–204 (1982).
Kiss and Baldauf, Gene 21: 111–119, (1983).
Walder et al., J. Biol. Chem. 258: 1235–1241, (1983).
Fomenkov et al., Nucl. Acids Res. 22: 2399–2403, (1994).
Malone et al., J. Mol. Biol. 253: 618–632, (1995).
New England Biolabs' Catalog, Jan. 2000, p. 220.
Kong, et al., Nucl. Acids. Res. 28:3216–3223 (2000).

*Primary Examiner*—Charles L. Patterson, Jr.
(74) *Attorney, Agent, or Firm*—Gregory D. Williams (57) ABSTRACT

The present invention relates to recombinant DNA coding for the MspA1I restriction endonuclease as well as MspA1I methylase, expression of MspA1I restriction endonuclease and MspA1I methylase in *E. coli* cells containing the recombinant DNA.

6 Claims, 4 Drawing Sheets

```
    ATGAGCCAAGCAATTAACTCTCCATTTCGCTATGCGGGTGGCAAATTCTACGCAAGAAAA
1   ------------+---------+---------+---------+---------+---------+ 60
    M  S  Q  A  I  N  S  P  F  R  Y  A  G  G  K  F  Y  A  R  K
    TTGATCCTCGAGCATGTTCCAGATCATACCTGTTACATAGAACCATTTGTAGGTGGCGGC
61  ------------+---------+---------+---------+---------+---------+ 120
    L  I  L  E  H  V  P  D  H  T  C  Y  I  E  P  F  V  G  G  G
    TCAATTTTCTTTGCAAAAGATAAAGTTGAGACAAATATTTTAAATGACGCTGATCCTGAT
121 ------------+---------+---------+---------+---------+---------+ 180
    S  I  F  F  A  K  D  K  V  E  T  N  I  L  N  D  A  D  P  D
    CTTATTAATACATACTTAATTATCAGAGATAGGGTTGATGAGCTGGTTGCTGCTTTAGAT
181 ------------+---------+---------+---------+---------+---------+ 240
    L  I  N  T  Y  L  I  I  R  D  R  V  D  E  L  V  A  A  L  D
    GGAGAGCAGGCTTTAAAAGAACGACATACTTGGTATAAGAATGAATTTAAGCCAACTAAT
241 ------------+---------+---------+---------+---------+---------+ 300
    G  E  Q  A  L  K  E  R  H  T  W  Y  K  N  E  F  K  P  T  N
    GAGCTAGAAAGAGCTGTACGTTGGTATTACTTAAATCGCACATCATACTCAGGAATTATG
301 ------------+---------+---------+---------+---------+---------+ 360
    E  L  E  R  A  V  R  W  Y  Y  L  N  R  T  S  Y  S  G  I  M
    AATCCTAAAAATTGTTATTGGGGGTATGGTGACAAATATAGTATGCGTCCAGAAAATTGG
361 ------------+---------+---------+---------+---------+---------+ 420
    N  P  K  N  C  Y  W  G  Y  G  D  K  Y  S  M  R  P  E  N  W
    GGTCGTAGCCTAATAAAAACATCGGCTAAATTACAAGGTGTTGAATTTACTAACCTTGAT
421 ------------+---------+---------+---------+---------+---------+ 480
    G  R  S  L  I  K  T  S  A  K  L  Q  G  V  E  F  T  N  L  D
    TTTGAGGATGTTATTGATAATGCACCTGATGGAGCATTCTTATTTGTAGATCCACCTTAC
481 ------------+---------+---------+---------+---------+---------+ 540
    F  E  D  V  I  D  N  A  P  D  G  A  F  L  F  V  D  P  P  Y
    TTCAATGCTGATCAAGATAAATTCTATACGTTCTCTTTTAAGAAGGAAGATCATTATCGC
541 ------------+---------+---------+---------+---------+---------+ 600
    F  N  A  D  Q  D  K  F  Y  T  F  S  F  K  K  E  D  H  Y  R
    TTAGAACAGTGTTTATTAAGAAATAAAGGACGTCTATCTTTCTTAATTACTTATGATAAT
601 ------------+---------+---------+---------+---------+---------+ 660
    L  E  Q  C  L  L  R  N  K  G  R  L  S  F  L  I  T  Y  D  N
    AGTCCTGAAATTAGGGAGTTATATTCTTGGGCTAATGCGCTGTTAGACAAAGAGTGGAAT
661 ------------+---------+---------+---------+---------+---------+ 720
    S  P  E  I  R  E  L  Y  S  W  A  N  A  L  L  D  K  E  W  N
    TATACAATTAGTAGAACTGATGATCAGACGAAGAATAAGAGTCAGGCTCCTGAAAAGGCA
721 ------------+---------+---------+---------+---------+---------+ 780
    Y  T  I  S  R  T  D  D  Q  T  K  N  K  S  Q  A  P  E  K  A
    TCTCGTTATAAAGGGAAAGAAGTATTTATAACGAATTATCAAGTAAAGGAGCCTGAAATT
781 ------------+---------+---------+---------+---------+---------+ 840
    S  R  Y  K  G  K  E  V  F  I  T  N  Y  Q  V  K  E  P  E  I
    TCTGAAAATTTAGAATTAACCTTCGATGAAGTTTAA
841 ------------+---------+---------+------ 876
    S  E  N  L  E  L  T  F  D  E  V  *
```

FIG. 3

```
     ATGAATCAGGAACTTATAGATTTTTGTGAACTATATAATCTACCTTTAGAACATTTAGGG
1    ---------+---------+---------+---------+---------+---------+ 60
     M  N  Q  E  L  I  D  F  C  E  L  Y  N  L  P  L  E  H  L  G

GCAACATTAAAAGATCCAAAAGTCATTCCAATGATTAGAGGAAAAGCTTTTGAATTTTCT
61   ---------+---------+---------+---------+---------+---------+ 120
     A  T  L  K  D  P  K  V  I  P  M  I  R  G  K  A  F  E  F  S

GTCAAAGATAGATTATCCCAAGTCCTTAATCAGAATATATGGCATGTATCTAAACCATTC
121  ---------+---------+---------+---------+---------+---------+ 180
     V  K  D  R  L  S  Q  V  L  N  Q  N  I  W  H  V  S  K  P  F

GTAAATCCACAATTAGGAAGCCATGACCAAGACGTACTTATCAAGCATCTACCGACAAAT
181  ---------+---------+---------+---------+---------+---------+ 240
     V  N  P  Q  L  G  S  H  D  Q  D  V  L  I  K  H  L  P  T  N

ACAGAAATTACTATCGAATGTAAATTGTCAGCTAAAGGACAATATAAATTTCAGACAAAT
241  ---------+---------+---------+---------+---------+---------+ 300
     T  E  I  T  I  E  C  K  L  S  A  K  G  Q  Y  K  F  Q  T  N

GAAAGTATTTTTAAAATCAAGTGTATGCGCAGTCGAACTCTAGGCCCAGAGTTAGTACGT
301  ---------+---------+---------+---------+---------+---------+ 360
     E  S  I  F  K  I  K  C  M  R  S  R  T  L  G  P  E  L  V  R

CGTTTAGCTCCACTTCGGGGAATGTCTGAAGAAAGTTTAAGTGTTCATAATGATCAATAT
361  ---------+---------+---------+---------+---------+---------+ 420
     R  L  A  P  L  R  G  M  S  E  E  S  L  S  V  H  N  D  Q  Y

TTAGTTGGTGATTTTGACTTAGTAATCACTTCACTTGCTAATGCATTCTATAGCACGAAT
421  ---------+---------+---------+---------+---------+---------+ 480
     L  V  G  D  F  D  L  V  I  T  S  L  A  N  A  F  Y  S  T  N

GAAGATGGAATCTTTGTTTGGGATCCATCAGCCTTAGGACAAAGCTTCCTTGAACAAAAA
481  ---------+---------+---------+---------+---------+---------+ 540
     E  D  G  I  F  V  W  D  P  S  A  L  G  Q  S  F  L  E  Q  K

TATGGTGTTGGGCTAAGTGAAAAACAGTATCAAGATGCTGCTTTCAATGATATGTACGTT
541  ---------+---------+---------+---------+---------+---------+ 600
     Y  G  V  G  L  S  E  K  Q  Y  Q  D  A  A  F  N  D  M  Y  V

GCTAGGGCTAGTGATTTAATTATTTCAGAAACAAATGAGGTTCTTTGCACAAGAAAGAAA
601  ---------+---------+---------+---------+---------+---------+ 660
     A  R  A  S  D  L  I  I  S  E  T  N  E  V  L  C  T  R  K  K

TGCTCTAATAATCAAAACTGTGGATTTATACCAAATTATCCGTTGTTAAAATTTAATCAT
661  ---------+---------+---------+---------+---------+---------+ 720
     C  S  N  N  Q  N  C  G  F  I  P  N  Y  P  L  L  K  F  N  H

AATAATTTAACAAACCCATCTAATAGATGGGTTCATATATCAAATATTGAAAACTTACTA
721  ---------+---------+---------+---------+---------+---------+ 780
     N  N  L  T  N  P  S  N  R  W  V  H  I  S  N  I  E  N  L  L

TTAAACTTCATCGAAGGTTAA
781  ---------+---------+- 801
     L  N  F  I  E  G  *
```

FIG. 4 ated with the overall cloning success. Experiment 1 concentrates on cloning 0.5–1.0 kb sized inserts, experiments 2 and 3 concentrate on cloning 1.0–2.0 kb sized inserts.

SEQUENCE LISTING

<160> NUMBER OF SEQ ID NOS: 14

<210> SEQ ID NO 1
<211> LENGTH: 876
<212> TYPE: DNA
<213> ORGANISM: Moraxella sp.
<220> FEATURE:
<221> NAME/KEY: CDS
<222> LOCATION: (1)..(876)
<223> OTHER INFORMATION:

<400> SEQUENCE: 1

```
atg agc caa gca att aac tct cca ttt cgc tat gcg ggt ggc aaa ttc      48
Met Ser Gln Ala Ile Asn Ser Pro Phe Arg Tyr Ala Gly Gly Lys Phe
1               5                   10                  15 tac gca aga aaa ttg atc ctc gag cat gtt cca gat cat acc tgt tac      96
Tyr Ala Arg Lys Leu Ile Leu Glu His Val Pro Asp His Thr Cys Tyr
                20                  25                  30 ata gaa cca ttt gta ggt ggc ggc tca att ttc ttt gca aaa gat aaa     144
Ile Glu Pro Phe Val Gly Gly Gly Ser Ile Phe Phe Ala Lys Asp Lys
            35                  40                  45 gtt gag aca aat att tta aat gac gct gat cct gat ctt att aat aca     192
Val Glu Thr Asn Ile Leu Asn Asp Ala Asp Pro Asp Leu Ile Asn Thr
        50                  55                  60 tac tta att atc aga gat agg gtt gat gag ctg gtt gct gct tta gat     240
Tyr Leu Ile Ile Arg Asp Arg Val Asp Glu Leu Val Ala Ala Leu Asp
65                  70                  75                  80 gga gag cag gct tta aaa gaa cga cat act tgg tat aag aat gaa ttt     288
Gly Glu Gln Ala Leu Lys Glu Arg His Thr Trp Tyr Lys Asn Glu Phe
                85                  90                  95 aag cca act aat gag cta gaa aga gct gta cgt tgg tat tac tta aat     336
Lys Pro Thr Asn Glu Leu Glu Arg Ala Val Arg Trp Tyr Tyr Leu Asn
                100                 105                 110 cgc aca tca tac tca gga att atg aat cct aaa aat tgt tat tgg ggg     384
Arg Thr Ser Tyr Ser Gly Ile Met Asn Pro Lys Asn Cys Tyr Trp Gly
            115                 120                 125 tat ggt gac aaa tat agt atg cgt cca gaa aat tgg ggt cgt agc cta     432
Tyr Gly Asp Lys Tyr Ser Met Arg Pro Glu Asn Trp Gly Arg Ser Leu
        130                 135                 140 ata aaa aca tcg gct aaa tta caa ggt gtt gaa ttt act aac ctt gat     480
Ile Lys Thr Ser Ala Lys Leu Gln Gly Val Glu Phe Thr Asn Leu Asp
145                 150                 155                 160 ttt gag gat gtt att gat aat gca cct gat gga gca ttc tta ttt gta     528
Phe Glu Asp Val Ile Asp Asn Ala Pro Asp Gly Ala Phe Leu Phe Val
                165                 170                 175 gat cca cct tac ttc aat gct gat caa gat aaa ttc tat acg ttc tct     576
Asp Pro Pro Tyr Phe Asn Ala Asp Gln Asp Lys Phe Tyr Thr Phe Ser
                180                 185                 190 ttt aag aag gaa gat cat tat cgc tta gaa cag tgt tta tta aga aat     624
Phe Lys Lys Glu Asp His Tyr Arg Leu Glu Gln Cys Leu Leu Arg Asn
            195                 200                 205 aaa gga cgt cta tct ttc tta att act tat gat aat agt cct gaa att     672
Lys Gly Arg Leu Ser Phe Leu Ile Thr Tyr Asp Asn Ser Pro Glu Ile
        210                 215                 220 agg gag tta tat tct tgg gct aat gcg ctg tta gac aaa gag tgg aat     720
Arg Glu Leu Tyr Ser Trp Ala Asn Ala Leu Leu Asp Lys Glu Trp Asn
225                 230                 235                 240 tat aca att agt aga act gat gat cag acg aag aat aag agt cag gct     768
Tyr Thr Ile Ser Arg Thr Asp Asp Gln Thr Lys Asn Lys Ser Gln Ala
                245                 250                 255
```

```
cct gaa aag gca tct cgt tat aaa ggg aaa gaa gta ttt ata acg aat        816
Pro Glu Lys Ala Ser Arg Tyr Lys Gly Lys Glu Val Phe Ile Thr Asn
        260                 265                 270 tat caa gta aag gag cct gaa att tct gaa aat tta gaa tta acc ttc        864
Tyr Gln Val Lys Glu Pro Glu Ile Ser Glu Asn Leu Glu Leu Thr Phe
    275                 280                 285 gat gaa gtt taa                                                        876
Asp Glu Val
    290

<210> SEQ ID NO 2
<211> LENGTH: 291
<212> TYPE: PRT
<213> ORGANISM: Moraxella sp.

<400> SEQUENCE: 2

Met Ser Gln Ala Ile Asn Ser Pro Phe Arg Tyr Ala Gly Gly Lys Phe
1               5                   10                  15

Tyr Ala Arg Lys Leu Ile Leu Glu His Val Pro Asp His Thr Cys Tyr
            20                  25                  30

Ile Glu Pro Phe Val Gly Gly Gly Ser Ile Phe Phe Ala Lys Asp Lys
        35                  40                  45

Val Glu Thr Asn Ile Leu Asn Asp Ala Asp Pro Asp Leu Ile Asn Thr
    50                  55                  60

Tyr Leu Ile Ile Arg Asp Arg Val Asp Glu Leu Val Ala Ala Leu Asp
65                  70                  75                  80

Gly Glu Gln Ala Leu Lys Glu Arg His Thr Trp Tyr Lys Asn Glu Phe
                85                  90                  95

Lys Pro Thr Asn Glu Leu Glu Arg Ala Val Arg Trp Tyr Tyr Leu Asn
            100                 105                 110

Arg Thr Ser Tyr Ser Gly Ile Met Asn Pro Lys Asn Cys Tyr Trp Gly
        115                 120                 125

Tyr Gly Asp Lys Tyr Ser Met Arg Pro Glu Asn Trp Gly Arg Ser Leu
    130                 135                 140

Ile Lys Thr Ser Ala Lys Leu Gln Gly Val Glu Phe Thr Asn Leu Asp
145                 150                 155                 160

Phe Glu Asp Val Ile Asp Asn Ala Pro Asp Gly Ala Phe Leu Phe Val
                165                 170                 175

Asp Pro Pro Tyr Phe Asn Ala Asp Gln Asp Lys Phe Tyr Thr Phe Ser
            180                 185                 190

Phe Lys Lys Glu Asp His Tyr Arg Leu Glu Gln Cys Leu Leu Arg Asn
        195                 200                 205

Lys Gly Arg Leu Ser Phe Leu Ile Thr Tyr Asp Asn Ser Pro Glu Ile
    210                 215                 220

Arg Glu Leu Tyr Ser Trp Ala Asn Ala Leu Leu Asp Lys Glu Trp Asn
225                 230                 235                 240

Tyr Thr Ile Ser Arg Thr Asp Asp Gln Thr Lys Asn Lys Ser Gln Ala
                245                 250                 255

Pro Glu Lys Ala Ser Arg Tyr Lys Gly Lys Glu Val Phe Ile Thr Asn
            260                 265                 270

Tyr Gln Val Lys Glu Pro Glu Ile Ser Glu Asn Leu Glu Leu Thr Phe
        275                 280                 285

Asp Glu Val
    290
```

```
<210> SEQ ID NO 3
<211> LENGTH: 801
<212> TYPE: DNA
<213> ORGANISM: Moraxella sp.
<220> FEATURE:
<221> NAME/KEY: CDS
<222> LOCATION: (1)..(801)
<223> OTHER INFORMATION:

<400> SEQUENCE: 3 atg aat cag gaa ctt ata gat ttt tgt gaa cta tat aat cta cct tta        48
Met Asn Gln Glu Leu Ile Asp Phe Cys Glu Leu Tyr Asn Leu Pro Leu
1               5                   10                  15 gaa cat tta ggg gca aca tta aaa gat cca aaa gtc att cca atg att        96
Glu His Leu Gly Ala Thr Leu Lys Asp Pro Lys Val Ile Pro Met Ile
            20                  25                  30 aga gga aaa gct ttt gaa ttt tct gtc aaa gat aga tta tcc caa gtc       144
Arg Gly Lys Ala Phe Glu Phe Ser Val Lys Asp Arg Leu Ser Gln Val
        35                  40                  45 ctt aat cag aat ata tgg cat gta tct aaa cca ttc gta aat cca caa       192
Leu Asn Gln Asn Ile Trp His Val Ser Lys Pro Phe Val Asn Pro Gln
    50                  55                  60 tta gga agc cat gac caa gac gta ctt atc aag cat cta ccg aca aat       240
Leu Gly Ser His Asp Gln Asp Val Leu Ile Lys His Leu Pro Thr Asn
65                  70                  75                  80 aca gaa att act atc gaa tgt aaa ttg tca gct aaa gga caa tat aaa       288
Thr Glu Ile Thr Ile Glu Cys Lys Leu Ser Ala Lys Gly Gln Tyr Lys
                85                  90                  95 ttt cag aca aat gaa agt att ttt aaa atc aag tgt atg cgc agt cga       336
Phe Gln Thr Asn Glu Ser Ile Phe Lys Ile Lys Cys Met Arg Ser Arg
            100                 105                 110 act cta ggc cca gag tta gta cgt cgt tta gct cca ctt cgg gga atg       384
Thr Leu Gly Pro Glu Leu Val Arg Arg Leu Ala Pro Leu Arg Gly Met
        115                 120                 125 tct gaa gaa agt tta agt gtt cat aat gat caa tat tta gtt ggt gat       432
Ser Glu Glu Ser Leu Ser Val His Asn Asp Gln Tyr Leu Val Gly Asp
    130                 135                 140 ttt gac tta gta atc act tca ctt gct aat gca ttc tat agc acg aat       480
Phe Asp Leu Val Ile Thr Ser Leu Ala Asn Ala Phe Tyr Ser Thr Asn
145                 150                 155                 160 gaa gat gga atc ttt gtt tgg gat cca tca gcc tta gga caa agc ttc       528
Glu Asp Gly Ile Phe Val Trp Asp Pro Ser Ala Leu Gly Gln Ser Phe
                165                 170                 175 ctt gaa caa aaa tat ggt gtt ggg cta agt gaa aaa cag tat caa gat       576
Leu Glu Gln Lys Tyr Gly Val Gly Leu Ser Glu Lys Gln Tyr Gln Asp
            180                 185                 190 gct gct ttc aat gat atg tac gtt gct agg gct agt gat tta att att       624
Ala Ala Phe Asn Asp Met Tyr Val Ala Arg Ala Ser Asp Leu Ile Ile
        195                 200                 205 tca gaa aca aat gag gtt ctt tgc aca aga aag aaa tgc tct aat aat       672
Ser Glu Thr Asn Glu Val Leu Cys Thr Arg Lys Lys Cys Ser Asn Asn
    210                 215                 220 caa aac tgt gga ttt ata cca aat tat ccg ttg tta aaa ttt aat cat       720
Gln Asn Cys Gly Phe Ile Pro Asn Tyr Pro Leu Leu Lys Phe Asn His
225                 230                 235                 240 aat aat tta aca aac cca tct aat aga tgg gtt cat ata tca aat att       768
Asn Asn Leu Thr Asn Pro Ser Asn Arg Trp Val His Ile Ser Asn Ile
                245                 250                 255 gaa aac tta cta tta aac ttc atc gaa ggt taa                           801
Glu Asn Leu Leu Leu Asn Phe Ile Glu Gly
            260                 265
```

```
<210> SEQ ID NO 4
<211> LENGTH: 266
<212> TYPE: PRT
<213> ORGANISM: Moraxella sp.

<400> SEQUENCE: 4

Met Asn Gln Glu Leu Ile Asp Phe Cys Glu Leu Tyr Asn Leu Pro Leu
1               5                   10                  15

Glu His Leu Gly Ala Thr Leu Lys Asp Pro Lys Val Ile Pro Met Ile
            20                  25                  30

Arg Gly Lys Ala Phe Glu Phe Ser Val Lys Asp Arg Leu Ser Gln Val
        35                  40                  45

Leu Asn Gln Asn Ile Trp His Val Ser Lys Pro Phe Val Asn Pro Gln
    50                  55                  60

Leu Gly Ser His Asp Gln Asp Val Leu Ile Lys His Leu Pro Thr Asn
65                  70                  75                  80

Thr Glu Ile Thr Ile Glu Cys Lys Leu Ser Ala Lys Gly Gln Tyr Lys
                85                  90                  95

Phe Gln Thr Asn Glu Ser Ile Phe Lys Ile Lys Cys Met Arg Ser Arg
            100                 105                 110

Thr Leu Gly Pro Glu Leu Val Arg Arg Leu Ala Pro Leu Arg Gly Met
        115                 120                 125

Ser Glu Glu Ser Leu Ser Val His Asn Asp Gln Tyr Leu Val Gly Asp
    130                 135                 140

Phe Asp Leu Val Ile Thr Ser Leu Ala Asn Ala Phe Tyr Ser Thr Asn
145                 150                 155                 160

Glu Asp Gly Ile Phe Val Trp Asp Pro Ser Ala Leu Gly Gln Ser Phe
                165                 170                 175

Leu Glu Gln Lys Tyr Gly Val Gly Leu Ser Glu Lys Gln Tyr Gln Asp
            180                 185                 190

Ala Ala Phe Asn Asp Met Tyr Val Ala Arg Ala Ser Asp Leu Ile Ile
        195                 200                 205

Ser Glu Thr Asn Glu Val Leu Cys Thr Arg Lys Lys Cys Ser Asn Asn
    210                 215                 220

Gln Asn Cys Gly Phe Ile Pro Asn Tyr Pro Leu Leu Lys Phe Asn His
225                 230                 235                 240

Asn Asn Leu Thr Asn Pro Ser Asn Arg Trp Val His Ile Ser Asn Ile
                245                 250                 255

Glu Asn Leu Leu Leu Asn Phe Ile Glu Gly
            260                 265

<210> SEQ ID NO 5
<211> LENGTH: 24
<212> TYPE: DNA
<213> ORGANISM: dna sequence adjacent to the M.MspA1I C-terminus

<400> SEQUENCE: 5
tgatatgtac gttgctaggg ctag                                          24

<210> SEQ ID NO 6
<211> LENGTH: 24
<212> TYPE: DNA
<213> ORGANISM: dna sequence adjacent to the M.MspA1I C-terminus

<400> SEQUENCE: 6
ttgaaagcag catcttgata ctgt                                          24
```

<210> SEQ ID NO 7
<211> LENGTH: 24
<212> TYPE: DNA
<213> ORGANISM: inverse PCR primers

<400> SEQUENCE: 7
tcacttcact tgctaatgca ttct                                   24

<210> SEQ ID NO 8
<211> LENGTH: 24
<212> TYPE: DNA
<213> ORGANISM: inverse PCR primers

<400> SEQUENCE: 8
ttactaagtc aaaatcacca acta                                   24

<210> SEQ ID NO 9
<211> LENGTH: 24
<212> TYPE: DNA
<213> ORGANISM: inverse PCR primers

<400> SEQUENCE: 9
attaggaagc catgaccaag acgt                                   24

<210> SEQ ID NO 10
<211> LENGTH: 24
<212> TYPE: DNA
<213> ORGANISM: inverse PCR primers

<400> SEQUENCE: 10
tgtggattta cgaatggttt agat                                   24

<210> SEQ ID NO 11
<211> LENGTH: 51
<212> TYPE: DNA
<213> ORGANISM: primers

<400> SEQUENCE: 11
aagcttgcat gcggaggtaa ataaatgaat caggaactta tagattttg t      51

<210> SEQ ID NO 12
<211> LENGTH: 51
<212> TYPE: DNA
<213> ORGANISM: primers

<400> SEQUENCE: 12
aagcttgcat gcggaggtga ttaaatgagc caagcaatta actctccatt t     51

<210> SEQ ID NO 13
<211> LENGTH: 54
<212> TYPE: DNA
<213> ORGANISM: primers

<400> SEQUENCE: 13
atcttaatac atatgggagg taaataaatg aatcaggaac ttatagattt ttgt  54

<210> SEQ ID NO 14
<211> LENGTH: 39

```
<212> TYPE: DNA
<213> ORGANISM: primers

<400> SEQUENCE: 14
aattatcaac atatggagcc tgaaatttct gaaaattta                                    39
```

METHOD FOR CLONING AND EXPRESSION OF MSPA1L RESTRICTION ENDONUCLEASE AND MSPA1L METHYLASE IN *E. COLI*

BACKGROUND OF THE INVENTION

The present invention relates to recombinant DNA that encodes the MspA1I restriction endonuclease (MspA1I endonuclease or MspA1I) as well as MspA1I methyltransferase (MspA1I methylase or M.MspA1I), expression of MspA1I endonuclease and methylase in *E. coli* cells containing the recombinant DNA.

MspA1I endonuclease is found in the strain of Moraxella species (NEB#775, New England Biolabs' strain collection). It recognizes the double-stranded DNA sequence 5'-CMG/CKG-3' (M=A or C; K=G or T, / indicates the cleavage position) and cleaves between the G and C to generate blunt ends. MspA1I methylase (M.MspA1I) is also found in the same strain, which recognizes the same DNA sequence and presumably modifies the cytosine at the N4 position on hemi-methylated or non-methylated MspA1I sites.

Type II restriction endonucleases are a class of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') along the DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and twenty-eight restriction endonucleases with unique specificities have been identified among the many hundreds of bacterial species that have been examined to date (Roberts and Macelis, *Nucl. Acids Res.* 29:268–269 (2001)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'-TTT/AAA-3', 5'-PuG/GNCCPy-3' and 5'-CACNNN/GTG-3' respectively. *Escherichia coli* RY13, on the other hand, produces only one Type II enzyme, EcoRI, which recognizes the sequence 5'-G/AATTC-3'.

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II restriction-modification systems have been cloned. The first cloning method used bacteriophage infection as a means of identifying or selecting restriction endonuclease clones (EcoRII: Kosykh et al., *Mol. Gen. Genet.* 178:717–719, (1980); HhaII: Mann et al., *Gene* 3:97–112, (1978); PstI: Walder et al., *Proc. Nat. Acad. Sci.* 78:1503–1507, (1981)). Since the expression of restriction-modification systems in bacteria enables them to resist infection by bacteriophages, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., *Nucl. Acids. Res.* 12: 3659–3676, (1984); PaeR7: Gingeras and Brooks, *Proc. Natl. Acad. Sci. USA* 80:402–406, (1983); Theriault and Roy, *Gene* 19:355–359 (1982); PvuII: Blumenthal et al., *J. Bacteriol.* 164:501–509, (1985); Msp45I: Wayne et al. *Gene* 202:83–88, (1997)).

A third approach is to select for active expression of methylase genes (methylase selection) (U.S. Pat. No. 5,200, 333 and BsuRI: Kiss et al., *Nucl. Acids. Res.* 13:6403–6421, (1985)). Since restriction-modification genes are often closely linked together, both genes can often be cloned simultaneously. This selection does not always yield a complete restriction system however, but instead yields only the methylase gene (BspRI: Szomolanyi et al., *Gene* 10:219–225, (1980); BcnI: Janulaitis et al., *Gene* 20:197–204 (1982); BsuRI: Kiss and Baldauf, *Gene* 21:111–119, (1983); and MspI: Walder et al., *J. Biol. Chem.* 258:1235–1241, (1983)).

A more recent method, the "endo-blue method", has been described for direct cloning of thermostable restriction endonuclease genes into *E. coli* based on the indicator strain of *E. coli* containing the dinD::lacZ fusion (Fomenkov et al., U.S. Pat. No. 5,498,535; Fomenkov et al., *Nucl. Acids Res.* 22:2399–2403, (1994)). This method utilizes the *E. coli* SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535). The disadvantage of this method is that some positive blue clones containing a restriction endonuclease gene are difficult to culture due to the lack of the cognate methylase gene.

There are three major groups of DNA methyltransferases based on the position and the base that is modified (C5 cytosine methylases, N4 cytosine methylases, and N6 adenine methylases). N4 cytosine and N6 adenine methylases are amino-methyltransferases (Malone et al. *J. Mol. Biol.* 253:618–632, (1995)). When a restriction site on DNA is modified (methylated) by the methylase, it is resistant to digestion by the cognate restriction endonuclease. Sometimes methylation by a non-cognate methylase can also confer DNA sites resistant to restriction digestion. For example, Dcm methylase modification of 5'-CCWGG-3' (W=A or T) can also make the DNA resistant to PspGI restriction digestion. Another example is that CpG methylase can modify the CG dinucleotide and make the NotI site (5'-GCGGCCGC-3') refractory to NotI digestion (New England Biolabs' catalog, 2000-01, page 220; Beverly, Mass.). Therefore methylases can be used as a tool to modify certain DNA sequences and make them uncleavable by restriction enzymes.

Type II methylase genes have been found in many sequenced microbial genomes (GenBank, REBASE™ (New England Biolabs, Inc., Beverly, Mass.)). Direct PCR cloning and over-expression of ORFs adjacent to the methylase genes resulted in discovery of novel restriction enzyme specificities (Kong, et al., *Nucl. Acid Res.* 28:3216–3223 (2000)).

Because purified restriction endonucleases and modification methylases are useful tools for creating recombinant molecules in the laboratory, there is a strong commercial interest to obtain bacterial strains through recombinant DNA techniques that produce large quantities of restriction enzymes and methylases. Such over-expression strains should also simplify the task of enzyme purification.

SUMMARY OF THE INVENTION

The present invention relates to a method for cloning MspA1I restriction gene (mspA1IR) from Moraxella species into *E. coli* by multiple inverse PCR and direct PCR from genomic DNA using primers that were based on the DNA sequences obtained via methylase selection.

It proved difficult to clone mspA1IR by screening a partial ApoI genomic DNA library. A second partial ApoI library was constructed using purified ApoI DNA fragments in the range of 3 to 10 kb. No positive methylase clones were ever identified. More complete genomic DNA libraries such as BamHI, EcoRI, HindIII, KpnI, SacI, SalI, SphI, and XbaI libraries were constructed and challenged with MspA1I endonuclease. Two resistant clones were identified with inserts encoding the MspA1I methylase in the BamHI library. The entire insert was sequenced. About 1900-bp sequence was derived upstream of the mspA1IM gene, but no apparent large ORFs were found that potentially encode the MspA1I endonuclease.

There is one truncated ORF of 281 bp downstream of the mspA1IM gene. This ORF did not show significant homology to any genes in GenBank. Therefore, efforts were made to obtain the sequence further downstream. After three rounds of inverse PCR reactions and direct sequencing of the PCR product, one ORF of 801 bp was found. This ORF, organized in the tail-to-tail orientation with the methylase gene, was the putative mspA1IR gene.

To over-express the putative mspA1IR gene and mspA1IM gene together in the same cell, both genes were amplified in PCR and cloned into expression vector pRRS. After screening 40 cell extracts of transformants, no over-expressing clones of MspA1I were detected. It was concluded that either the clones did not contain any insert, or did contain insert but expressed poorly due to under-methylation, or mutation(s) in the mspA1IR gene introduced in PCR. It was determined that a two-plasmid expression system may be more productive in over-expression of MspA1I.

Plasmid pUC19-MspA1IM was first introduced into T7 expression host ER2566 to fully modify the host chromosome. The mspA1IR gene was amplified by low cycles of PCR and inserted into a low-copy-number T7 expression vector pACYC-T7ter. The expression strain was ER2566 [pUC19-MspA1IM, pACYC-T7ter-MspA1IR]. After screening 25 cell extracts, 6 MspA1I over-expression clones were found. The mspA1IR insert of two expression clones were sequenced and confirmed to contain the same wild type sequence.

BRIEF DESCRIPTION OF THE DRAWINGS

FIG. 2. MspA1I methylase gene sequence (mspA1IM, 876 bp) (SEQ ID NO:1) and the encoded amino acid sequence (SEQ ID NO:2).

FIG. 3. MspA1I endonuclease gene sequence (mspA1IR, 801 bp) (SEQ ID NO:3) and the encoded amino acid sequence (SEQ ID NO:4).

DETAILED DESCRIPTION OF THE INVENTION

It proved difficult to clone the mspA1IM gene by screening ApoI partial genomic DNA libraries. The mspA1IM gene must have been destroyed by the limited ApoI partial digestion. To increase the chances of survival after restriction digestion, some 6-base cutting restriction enzymes such as BamHI and EcoRI were chosen to construct more genomic DNA libraries. The mspA1IM gene was cloned by the methylase selection from the BamHI library. The entire mspA1IM gene was sequenced. No significant ORFs were found upstream of the mspA1IM gene within ~1900 bp sequence. A small truncated ORF about 281 bp was found downstream. Therefore, more efforts were made to amplify and sequence the downstream DNA sequences. After three rounds of inverse PCR, an ORF of 801 bp was found and this gene was named mspA1IR.

It turned out that it was difficult to express mspA1IM and mspA1IR genes together in a single plasmid, probably due to the convergent gene organization of R-M genes. In order to express mspA1IR and mspA1IM genes together in the same cell, both genes were amplified in a PCR reaction. The PCR product was digested with SphI, purified, and ligated to CIP treated pRRS with compatible ends. The ligated DNA was transferred into ER2683 (RecA$^+$) and ER2688 (RecA$^-$) by transformation (ER2683 and ER2688 (New England Biolabs, Inc. Collection; Beverly, Mass.)). Cell lysates from forty 10-ml IPTG-induced cultures were screened for MspA1I activity. However, No apparent MspA1I activity was detected. Finally, a two-plasmid expression system was used to highly express the mspA1IR gene in *E. coli*.

The method described herein by which the MspA1I methylase gene (mspA1IM) and the MspA1I restriction gene (mspA1IR) are preferably cloned and expressed in *E. coli* using the following steps:

1. Construction of Genomic DNA Libraries

Moraxella sp. genomic DNA was digested completely with BamHI, EcoRI, HindIII, KpnI, SacI, SalI, SphI, and XbaI, respectively. The restricted DNA was purified and ligated to linear CIP treated pUC19 with compatible ends. To test the efficiency of ligation of the inserts, transformants were plated on LB agar plates with Ap+X-gal+IPTG and white colonies were scored. About 80% colonies were white and presumably contained inserts (disruption of the lacZα gene resulted in white colony phenotype). About 5,000 $Ap^R$ transformants were derived from the BamHI complete library. The BamHI library and the remaining EcoRI, HindIII, KpnI, SacI, SalI, SphI, XbaI libraries (2,000 to 5,000 colonies in each library) were combined and amplified in 2.2 L LB+Ap overnight. Plasmid DNA library was prepared.

2. Cloning of mspA1IM Gene by Methylase Selection

Varying amounts of the plasmid library DNA were challenged with MspA1I overnight. The MspA1I-digested DNA was used to transform ER2683 competent cells. Thirty-six plasmids were prepared from the cultures of transformants and screened for resistance to MspA1I digestion. Among the 36 screened, two plasmids (#5 and #24) were resistant to MspA1I digestion. Restriction mapping indicated that the insert was about 3 kb. The insert was sequenced using pUC universal primers and custom-made primers. The M.MspA1I is an N4 cytosine methylase that shows extensive homology to other α type amino-methyltransferases.

3. Inverse PCR Amplification of DNA Downstream of MspA1I Methylase

Figure 1:
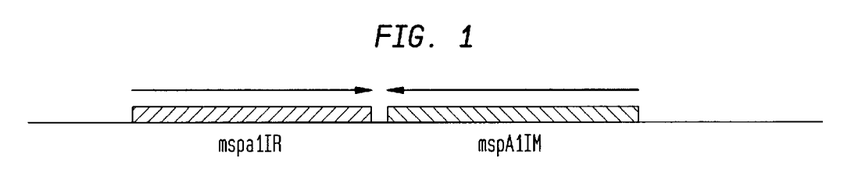
FIG. 1. Gene organization of MspA1I R-M system. mspA1IR, MspA1I restriction endonuclease gene; mspA1IM, MspA1I methylase gene.

After identification of the mspA1IM gene, efforts were made to clone adjacent DNA. No significant open reading frames (ORFs) were found upstream of the M gene (upstream of the M.MspA1I N-terminus coding sequence). Since restriction and modification genes in a particular R-M system are usually located less than 1 kb apart, efforts were made to clone the downstream sequence (DNA sequence adjacent to the M.MspA1I C-terminus coding sequence). After three rounds of inverse PCR and direct sequencing of the inverse PCR products, an ORF with 801 bp long was found downstream of the M.MspA1I gene. This gene was most likely the restriction gene (mspA1IR) encoding MspA1I. Transcription of the R and M genes converge, since they are arranged in tail-to-tail fashion (see FIG. 1 for gene organization).

4. Expression of mspA1IR Gene in E. coli

A two-plasmid expression system was employed for overexpression. The plasmid isolated in the original methylase selection pUC19-MspA1IM was first introduced into the T7 expression host ER2566 to fully modify the chromosomal DNA.

Figure 4:
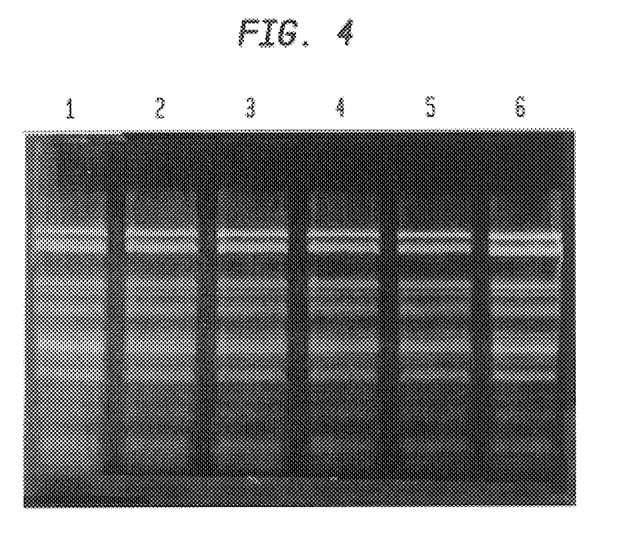
FIG. 4. Recombinant MspA1I endonuclease activity in cell extract. λDNA was used as the substrate. Lanes 1–5, 1/100, 1/200, 1/400, 1/800, 1/1600-fold dilution of cell extract added in the restriction digestions. Lane 6, λDNA cleaved with native MspA1I.

PCR conditions were optimized at 6 mM $Mg^{++}$ concentration for amplification of mspA1IR gene from the genomic DNA. PCR DNA containing mspA1IR gene was amplified and purified. Following restriction digestion with NdeI, the PCR DNA was ligated to CIP treated pACYC-T7ter with compatible ends. The ligated DNA was transformed into pre-modified host ER2566 [pUC19-MspA1IM]. IPTG-induced cell cultures were made from the co-transformants and cell extracts prepared by sonication. Clarified lysates were assayed for MspA1I endonuclease activity on λDNA substrate. Six highly active MspA1I-producing clones were found after screening 25 IPTG-induced cell extracts. Five partially active MspA1I-producing clones were also found, suggesting mutation(s) introduced in PCR amplification. The MspA1I activity of one active clone is shown in FIG. 4.

It was thus confirmed that the ORF adjacent to mspA1IM gene is the bona fide mspA1IR gene, encoding active MspA1I endonuclease.

The plasmid DNA pACYC-T7ter-MspA1IR clone #7 was prepared by Qiagen mini-spin column and the entire insert was sequenced. The insert contains the wild type (WT) coding sequence.

EXAMPLE 1

Cloning of MspA1I Restriction-Modification System in E. coli

1. Preparation of Genomic DNA

Genomic DNA was prepared from 8 g of Moraxella sp. (NEB #775, New England Biolabs collection) by the standard procedure consisting of the following steps:

a. Cell lysis by addition of lysozyme (2 mg/ml final), sucrose (1% final), and 50 mM Tris-$HCl_1$, pH 8.0.

b. Further cell lysis by addition of SDS at a final concentration of 0.1%.

c. Further cell lysis by addition of 1% Triton X-100, 62 mM EDTA, 50 mM Tris-HCl, pH 8.0.

d. Removal of proteins by phenol-$CHCl_3$ extraction of DNA 3 times (equal volume) and $CHCl_3$ extraction once.

e. Dialysis in 4 liters of TE buffer, buffer change twice.

f. RNase A treatment to remove RNA.

g. Genomic DNA precipitation in 95% ethanol, centrifuged, washed, dried and resuspended in TE buffer.

2. Restriction Digestion of Genomic DNA and Construction of Genomic DNA Library

Restriction enzyme ApoI was diluted by 2-fold serial dilutions (8, 4, and 2 units). Twenty μg of Moraxella sp. genomic DNA was digested partially with ApoI and partial digestion was achieved by 8 and 4 units of ApoI. The ApoI digested DNA was ligated to EcoRI digested and CIP treated pRRS vector that contains multiple MspA1I sites. The vector pRRS is a high-copy-number plasmid for cloning and expression of genes in E. coli. Following overnight ligation, the ligated DNA was used to transform an endA⁻ RR1 competent cells (ER2502) by electroporation. Approximately 5,000 $Ap^R$ transformants were obtained for the ApoI partial library. All the colonies were pooled and amplified in 1 liter LB+Ap overnight. Plasmid DNA was prepared by Qiagen Maxi-prep columns, resulting in ApoI #1 library. The primary plasmid DNA library (0.25 μg, 0.5 μg, 1 μg, 2 μg DNA) was challenged with MspA1I digestion overnight. The digested DNA was transferred into ER2502 by transformation. Nine $Ap^R$ survivors were found and plasmid DNA was prepared from the overnight cell cultures. After digestion with MspA1I, no true resistant clones were found.

A second ApoI partial genomic DNA library was constructed. Following ApoI digestion of the genomic DNA, DNA fragments in the range of 3–10 kb were gel-purified from a low-melting agarose gel and then ligated to pRRS with compatible ends. ApoI partial genomic DNA library (ApoI #2 library) was constructed and challenged the same way as described above. A complexity of >5000 colonies in the library were obtained. No MspA1I resistant clones were found. The failure to clone the mspA1IM gene in the two ApoI libraries suggested that there were multiple ApoI sites in the mspA1IM gene and the gene might be destroyed after partial digestion. To prevent digestion of the mspA1IM gene, 6-base cutting restriction fragments were chosen for construction of more genomic libraries.

To construct complete genomic DNA library, Moraxella sp. genomic DNA was digested with BamHI, EcoRI, HindIII, KpnI, SacI, SalI, SphI, XbaI, respectively at 37° C. for 3 h. The restricted DNA was then purified via phenol-CHCl₃ extraction and ethanol precipitation and the DNA pellet resuspended in TE buffer. They were ligated to linear CIP treated pUC19 with compatible ends. To ensure construction of a good quality genomic DNA library (clones with inserts), ER2683 transformants were plated on Ap+X-gal+IPTG plates and incubated overnight at 37° C. White colonies were scored among the blue background, assuming white colonies carryings plasmids with inserts due to the disruption of the lacZα gene in the multiple cloning sites of pUC19. Approximately 80% of colonies were white, indicating that a large percent of clones contained inserts. About 5,000 AP^R transformants were derived from the BamHI complete library. The BamHI complete library and the remaining EcoRI, HindIII, KpnI, SacI, SalI, SphI, XbaI libraries were combined and amplified in 2.2 L LB+Ap overnight. Plasmid DNA was prepared by the Qiagen Maxi column method.

3. Cloning of mspA1IM Gene by Methylase Selection

Varying amount of the plasmid library DNA (0.125, 0.25 μg, 0.5 μg, 1 μg) was challenged with MspA1I overnight at 37° C. The MspA1I-digested DNA was used to transform ER2683 competent cells. More than 100 Ap^R survivor transformants were obtained. Thirty-six plasmids were prepared from 1.5 ml cell cultures inoculated from the transformants and screened for resistance to MspA1I digestion. Among the 36 screened, two plasmids (#5 and #24) were found to be resistant to MspA1I digestion. For restriction mapping of the insert, #24 plasmid was digested with restriction enzymes ApoI, BamHI, EcoRI, HincII, HindIII, KpnI, PstI, SacI, SalI, SphI, and XbaI, respectively. The insert size was estimated to be about 3 kb. The clone with the insert was derived from the BamHI library. The insert was sequenced using pUC universal primers and custom-made primers (NEB organic synthesis). The MspA1I methylase is an N4 cytosine methylase that shows extensive homology to other amino-methyltransferases.

4. Inverse PCR Amplification of DNA Downstream of MspA1I Methylase

After identification of the methylase gene, efforts were made to clone adjacent DNA. No significant ORFs were found upstream of the methylase gene within about 1900 bp sequence (upstream of the M.MspA1I N-terminus coding sequence). Since restriction and modification genes in a particular R-M system are usually located in close proximity to each other, efforts were made to clone the downstream sequence (DNA sequence adjacent to the M.MspA1I C-terminus coding sequence)

Two primers were synthesized with the following sequences:

```
                                        (SEQ ID NO:5)
    5-'tgatatgtacgttgctagggctag-3'         (266-111)

(SEQ ID NO:6)
    5'-ttgaaagcagcatcttgatactgt-3'         (266-112)
```

The genomic DNA was digested with AatII, ApoI, BclI, BsaHI, HhaI, HinPlI, NdeI, PsiI, SspI, and XcmI, respectively. The digested DNA was purified through Qiagen spin columns. Self-ligation was set up at a low DNA concentration at 2 μg/ml overnight at 16° C. T4 DNA ligase was inactivated at 65° C. for 30 min and the circular DNA was precipitated by ethanol. 0.1–0.2 μg of the ligated products were used as the template for inverse PCR. PCR conditions were 94° C. for 2 min, 1 cycle; 94° C. for 1 min, 60° C. for 1 min, 72° C. for 2 min for 35 cycles. A small PCR product (~300 bp) was found in the SspI template. The PCR product was purified from a low-melting agarose gel and sequenced directly with primers 266-111 and 266-112. The entire SspI fragment was sequenced, generating 85 bp of new sequence downstream. Genomic DNA was also digested with AciI, AflII, BsaBI, BspHI, BstNI, ClaI, DraI, EaeI, EcoRI, HaeII, HaeIII, HpaI, KpnI, MscI, and SacI, respectively. The digested DNA was self-ligated at a low concentration and then used as templates for inverse PCR. Despite tremendous efforts no apparent large PCR products were detected. It was concluded that a second set of inverse PCR primers were needed for further inverse PCR walking.

A second set of inverse PCR primers were synthesized with the following sequences:

```
                                        (SEQ ID NO:7)
    5'-tcacttcacttgctaatgcattct-3'         (268-61)

(SEQ ID NO:8)
    5'-ttactaagtcaaaatcaccaacta-3'         (268-62)
```

The genomic DNA was digested with AatII, AluI, ApoI, BamHI, BclI, BstYI, DraI, HhaI, HindIII, MboI, MseI, NlaIII, NspI, PsiI, RsaI, TaqI, Tsp509I, and XhoI, respectively. The digested DNA was purified through Qiagen spin columns. Self-ligation was set up at a low DNA concentration at 2 μg/ml overnight at 16° C. T4 DNA ligase was inactivated at 65° C. for 30 min and the circular DNA was precipitated by ethanol. 0.1–0.2 μg of the ligated products were used as the template for inverse PCR. PCR conditions were 94° C. for 2 min, 1 cycle; 94° C. for 30 sec, 55° C. for 30 sec, 72° C. 2 min for 40 cycles. PCR products were found in NlaIII and NspI templates. The PCR products were purified from a low-melting agarose gel and sequenced with primers 268-61 and 62. The entire PCR fragments were sequenced, generating ~254 bp of new sequence downstream. Because type II restriction genes are in the range of ~500 to 3000 bp, additional inverse PCR was necessary to obtain more coding sequence.

A third set of inverse PCR primers were made with the following sequence:

```
                                        (SEQ ID NO:9)
    5'-attaggaagccatgaccaagacgt-3'         (268-287)

(SEQ ID NO:10)
    5'-tgtggatttacgaatggtttagat-3'         (268-288)
```

The genomic DNA was digested with AatII, AluI, ApoI, BamHI, DraI, HaeIII, HhaI, HindIII, HinPlI, NsiI, NspI, RsaI, SspI, and TaqI, respectively. The digested DNA was purified through Qiagen spin columns. Self-ligation was set up at a low DNA concentration at 2 μg/ml overnight at 16° C. T4 DNA ligase was inactivated at 65° C. for 30 min and the circular DNA was precipitated by ethanol. 0.1–0.2 μg of the 1-gated products were used as the template for inverse PCR. PCR conditions were 94° C. for 2 min, 1 cycle; 94° C. for 30 sec, 55° C. for 30 sec, 72° C. 2 min for 40 cycles. PCR products were found in AluI, BamHI, DraI, HaeIII, HhaI, HindIII, HinPlI, NsiI, NspI, SspI, and TaqI templates. The PCR products of AluI, DraI, HinPlI, and NsiI were purified from a low-melting agarose gel and sequenced with primers Because a single plasmid expression failed to produce high expression of MspA1I, a two-plasmid expression system was employed. The plasmid isolated in the original methylase selection pUC19-MspA1IM was first introduced into T7 expression host ER2566 to fully modify the chromosomal DNA. Two PCR primers were made with the following sequences in order to amplify the mspA1IR gene:

```
5'-atcttaatacatatgggaggtaaataaatgaatcaggaacttatagattttt   (SEQ ID NO:13)
tgt-3'  (271–278, underlined nt = NdeI site).

5'-aattatcaacatatggagcctgaaatttctgaaaattta-3'             (SEQ ID NO:14)
(271–279, underlined nt = NdeI site).
```

268–287 and 288. The entire PCR fragments were sequenced, generating ~525 bp of new sequence downstream.

An ORF with 801 bp long was found downstream of the M.MspA1I. This gene was most likely the restriction gene (mspA1IR) coding for MspA1I. Transcription of R and M genes is oriented in opposite direction. They are arranged in tail-to-tail fashion (see FIG. 1 for gene organization).

EXAMPLE 2

Expression of mspA1IR Gene in E. coli

In order to express mspA1IR and mspA1IM genes together in the same cell, both genes were amplified in a PCR reaction using primers with the following sequences:

```
5'-aagcttgcatgcggaggtaaataaatgaatcaggaacttatagatttttgt-3'    (270–231) (SEQ ID NO:11)

5'-aagcttgcatgcggaggtgattaaatgagccaagcaattaactctccattt-3'    (270–232) (SEQ ID NO:12)
```

PCR conditions were 95° C. for 2 min, 1 cycle; 94° C. for 30 sec, 55° C. for 30 sec, 72° C. 2 min for 20 cycles. The PCR product was digested with SphI, purified by running through spin columns and ligated to CIP treated pRRS with compatible ends. Following ligation overnight, the DNA was transferred into ER2683 (RecA$^+$) and ER2688 (RecA$^-$) by transformation. Forty 10-ml cell cultures were made from individual Ap$^R$ transformants and grown to late log phase. IPTG induction continued for 3 h. Cell extracts were prepared by sonicatioon and centrifugation. The clarified lysate wad used for digestion of λDNA. However, No apparent MspA1I activity was detected. The negative result may be resulted from poor methylation or poor expression of endonuclease. In a separate experiment it was confirmed that two clones with inserts were partially resistant to MspA1I digestion. Since MspA1I R-M genes are convergent in organization (tail-to-tail fashion) only one of the genes is driven by the lac promoter ($P_{lac}$–M>R or $P_{lac}$–R>M). In this cloning strategy, it was wishfully expected that the M gene was driven by the lac promoter and R gene was in the opposite direction, resulting in more methylase expression than endonuclease expression. However, the experimental data did not support this hypothesis.

PCR conditions were 95° C. 2 min, 1 cycle; 94° C. for 30 sec, 55° C. for 30 sec, 72° C. for 2 min for 20 cycles with Vent DNA polymerase. Since Vent DNA polymerase is sensitive to Mg$^{++}$ concentration and generates variable product yield, efforts were made to optimize the PCR condition with the addition of extra MgSO$_4$. It was found that 2 and 4 mM MgSO$_4$ yielded very little PCR products whereas in 6 and 10 mM MgSO$_4$ there were large amount of PCR products. It was concluded that 6 mM was the optimal Mg$^{++}$ concentration for amplification the mspA1IR gene from the genomic DNA. More PCR DNA containing mspA1IR gene was amplified and purified by phenol-CH$_3$Cl extraction and CH$_3$Cl extraction, precipitated with ethanol, dried and resuspended in TE buffer. Following restriction digestion with NdeI and purification through Qiagen spin columns, the PCR DNA was ligated to CIP treated pACYC-T7ter with compatible ends. The ligated DNA was transformed into pre-modified host ER2566 [pUC19-MspA1IM]. The plasmid pUC19-MspA1IM was the original methylase positive clone isolated during methylase selection. Co-transformants were plated on LB agar plates with Ap (100 μg/ml) and Cm (33 μg/ml). Ten ml of cell cultures were made from individual transformants and grown to late log phase (~4 h at 37° C.). IPTG was added to the final concentration of 0.5 mM to induce expression of the target gene. After 3 h induction, cells were harvested by centrifugation and cell extracts were prepared by sonication. Clarified lysate was assayed for MspA1I endonuclease activity on λDNA substrate and then analyzed by agarose gel electrophoresis. Six highly active MspA1I-producing clones were found after screening 25 IPTG-induced cell extracts. Five partially active MspA1I-producing clones were also found, suggesting mutation(s) may have been introduced in PCR. The MspA1I activity of one active clone was shown in FIG. 4. It was confirmed that the ORF adjacent to mspA1IM gene is the bona fide mspA1IR gene, encoding active MspA1I endonuclease.

The plasmid DNA pACYC-T7ter-MspA1IR clone #7 was prepared by Qiagen min-spin column and the entire insert was sequenced. It was found that the insert contained the wild type coding sequence.

The strain NEB#1420 ER2566 [pUC19-MspA1IM, PACYC-T7ter-MspA1IR] has been deposited under the terms and conditions of the Budapest Treaty with the American Type Culture Collection on Feb. 5, 2002 and received ATCC Accession No. PTA-4046.

What is claimed is:

1. Isolated DNA encoding the MspA1I restriction endonuclease, wherein the isolated DNA is obtainable from ATCC No. PTA-4046.

2. A recombinant DNA vector comprising a vector into which a DNA segment encoding the MspA1I restriction endonuclease has been inserted.

3. Isolated DNA encoding the MspA1I restriction endonuclease and MspA1I methylase, wherein the isolated DNA is obtainable from ATCC No. PTA-4046.

4. Vectors that comprise the isolated DNA of claim 3.

5. A host cell transformed by the vector of claims 2 or 4.

6. A method of producing recombinant MspA1I restriction endonuclease comprising culturing a host cell transformed with the vector of claims 2 or 4 under conditions suitable for expression of said endonuclease.

* * * * *